(12) United States Patent
Cheng et al.

(10) Patent No.: US 7,579,028 B1
(45) Date of Patent: Aug. 25, 2009

(54) ALOE VERA GLOVE AND ITS MANUFACTURING METHOD

(76) Inventors: Yung Chu Cheng, 19F-3, No. 508, Chung Hsiao E. Rd., Sec. 5, Taipei (TW); Fung Bor Chen, 801 E. Silverleaf St., Greer, SC (US) 29650

( * ) Notice: Subject to any disclaimer, the term of this patent is extended or adjusted under 35 U.S.C. 154(b) by 488 days.

(21) Appl. No.: 10/865,794

(22) Filed: Jun. 14, 2004

(51) Int. Cl.
- *A61K 36/886* (2006.01)
- *A41D 19/00* (2006.01)
- *C08J 9/30* (2006.01)

(52) U.S. Cl. .............................. 424/744; 2/159; 521/65
(58) Field of Classification Search ............ None
See application file for complete search history.

(56) References Cited

U.S. PATENT DOCUMENTS 6,953,483 B2 * 10/2005 Litke et al. .................. 8/94.33

| | | | |
|---|---|---|---|
| 2002/0025335 A1 * | 2/2002 | Chou ......................... | 424/402 |
| 2004/0091504 A1 * | 5/2004 | Hamann ................. | 424/195.17 |
| 2004/0091519 A1 * | 5/2004 | Amdur, III .................. | 424/443 |
| 2004/0091557 A1 * | 5/2004 | Hamann ..................... | 424/727 |
| 2004/0122382 A1 * | 6/2004 | Johnson et al. ............. | 604/292 |

* cited by examiner

*Primary Examiner*—Christopher R. Tate
*Assistant Examiner*—Deborah A. Davis
(74) *Attorney, Agent, or Firm*—Troxell Law Office, PLLC

(57) ABSTRACT

An Aloe Vera glove manufacturing method is disclosed which uses a flow of compressed air to blow semi-finished inner-surface-out status gloves away from respective glove formers, and then covers a layer of Aloe Vera solution on the inner surface of each glove, and then has the Aloe Vera solution on the inner surface of each glove be dried by heating, and finally has the Aloe Vera-coated gloves be reversed to keep the layer of Aloe Vera coated inner surface of each glove face on the inside and the outer surface of each glove face on the outside.

5 Claims, 6 Drawing Sheets

ALOE VERA GLOVE AND ITS MANUFACTURING METHOD

BACKGROUND OF THE INVENTION

1. Field of the Invention

The present invention relates to a glove manufacturing method and more particularly, to an Aloe Vera glove manufacturing method, which is practical for manufacturing Aloe Vera gloves efficiently and economically.

2. Description of the Related Art

It is well known that Aloe Vera has active ingredients that can condition hand skin and prevent microorganisms from growing under the wet condition. Therefore, Aloe Vera has been intensively used in cosmetics and other products.

U.S. Pat. No. 6,589,544 discloses the use of multiple layers in the glove design to impregnate Aloe Vera in an elastomeric article. The Aloe Vera bound in the article is difficult to come out. Therefore, the effect of the impregnated Aloe Vera to condition the user's skin is questionable. The multiple layer design also makes production complicated and the cost of the product increased.

U.S. Pat. No. 6,630,152 describes a method of applying Aloe Vera onto a portion of the glove while the glove is on the former of a glove dipping machine. Existing glove dipping machines are difficult to modify and allocate enough space for another dipping or spraying station. Especially, the glove inner surface facing outward on the former in a machine is loaded with impurities from the blooming of natural rubber protein, coagulants, accelerators and compounding ingredients out of glove substrate during the glove making process. These impurities are very toxic to the user's skin and difficult completely to clean out on the machine before the application of Aloe Vera.

U.S. Pat. No. 6,274,154 discloses an Aloe Vera glove manufacturing method. This method comprises the steps of: (41) washing glove former, (42) drying glove former, (43) coagulant dipping, (44) coagulant drying, (45) latex dipping, (46) vulcanization, (47) adhesion-prevention treatment, (48) stripping, (49) outer surface chlorine treating, (50) glove surface reversing, (51) inner surface chlorine treating, (52) Aloe Vera coating, (53) drying, (54) glove surface reversing, (55) finished product.

This Aloe Vera glove manufacturing method is complicated. After removal of each glove from the respective glove former (48), each glove has the respective inner surface face inward and the respective outer surface face outward. After the outer surface chlorine treating (49), each glove is turned inside out to have the respective inner surface face outward and the respective outer surface face inward (50). And after the inner surface chlorine treating (51), Aloe Vera coating (52) and drying (53) steps, each glove must be turned inside out again to have the respective outer surface face outward and the respective inner surface face inward (54). Further, according to this manufacturing method, the finger portions of the outer surface of the glove are first to contact with chlorine solution in step 49. The finish glove (55) may have been over-treated with chlorine, thereby lowering the gripping power of the finger portions of the glove.

Therefore, it is desirable to provide an Aloe Vera glove manufacturing method that eliminates the aforesaid drawbacks.

SUMMARY OF THE INVENTION

The present invention has been accomplished under the circumstances in view. It is therefore the main object of the present invention to provide an Aloe Vera glove manufacturing method, which is simplifies the manufacturing of Aloe Vera gloves. It is another object of the present invention to provide an Aloe Vera glove manufacturing method, which greatly reduces Aloe Vera glove manufacturing cost and has the finger tip portions of the outer surface of the gloves maintain gripping power.

To achieve these and other objects of the present invention, the invention uses a flow of compressed air to blow semi-finished inner-surface-out status gloves directly away from respective glove formers, has the gloves chlorinated and then covers a layer of Aloe Vera solution on the inner surface of each glove, and then has the Aloe Vera solution on the inner surface of each glove be dried by heating, and finally has the Aloe Vera-coated gloves be reversed to keep the layer of Aloe Vera coated inner surface of each glove face on the inside and the outer surface of each glove face on the outside. Before stripping from the glove formers, the inner surface of each glove on the respective glove former faces outward, therefore the inner surface of each glove is maintained on the outside for quick chlorine treatment when removed from the respective glove former by a flow of compressed air. This method prevents overdone of chlorine treatment at the tips of the finger portions of the outer surface of the gloves. Therefore, when the users use the finished gloves to perform a medical operation, the finger portions of the finished gloves do not slip on holding, and the user can operate medical instruments safely. Because the procedure from stripping to the finished product is quite simple, the invention greatly improves the manufacturing efficiency and reduces the manufacturing cost. When in use, the layer of Aloe Vera is maintained in contact with the user's skin, and the active ingredients in Aloe Vera can then condition hand skin and prevent microorganisms from growing under the wet condition.

DETAILED DESCRIPTION OF THE INVENTION

Figure 1:
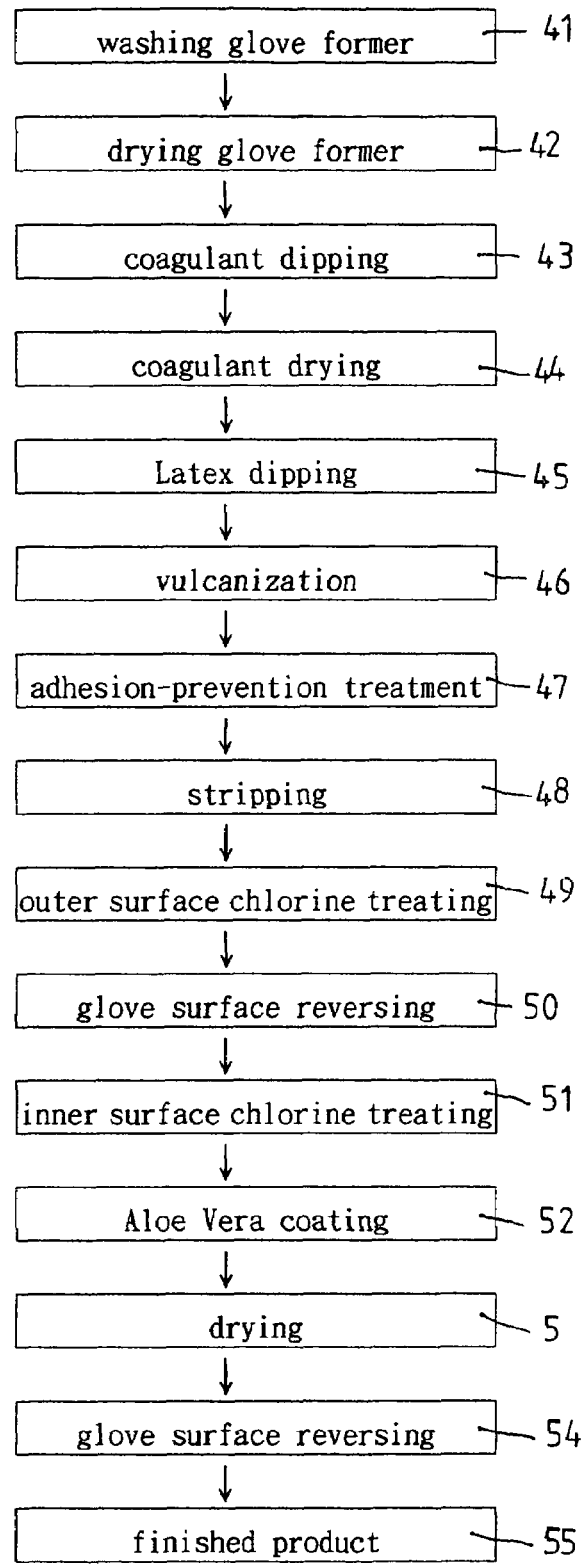
FIG. 1 is a block diagram showing a glove manufacturing flow according to the prior art.
Figure 2:
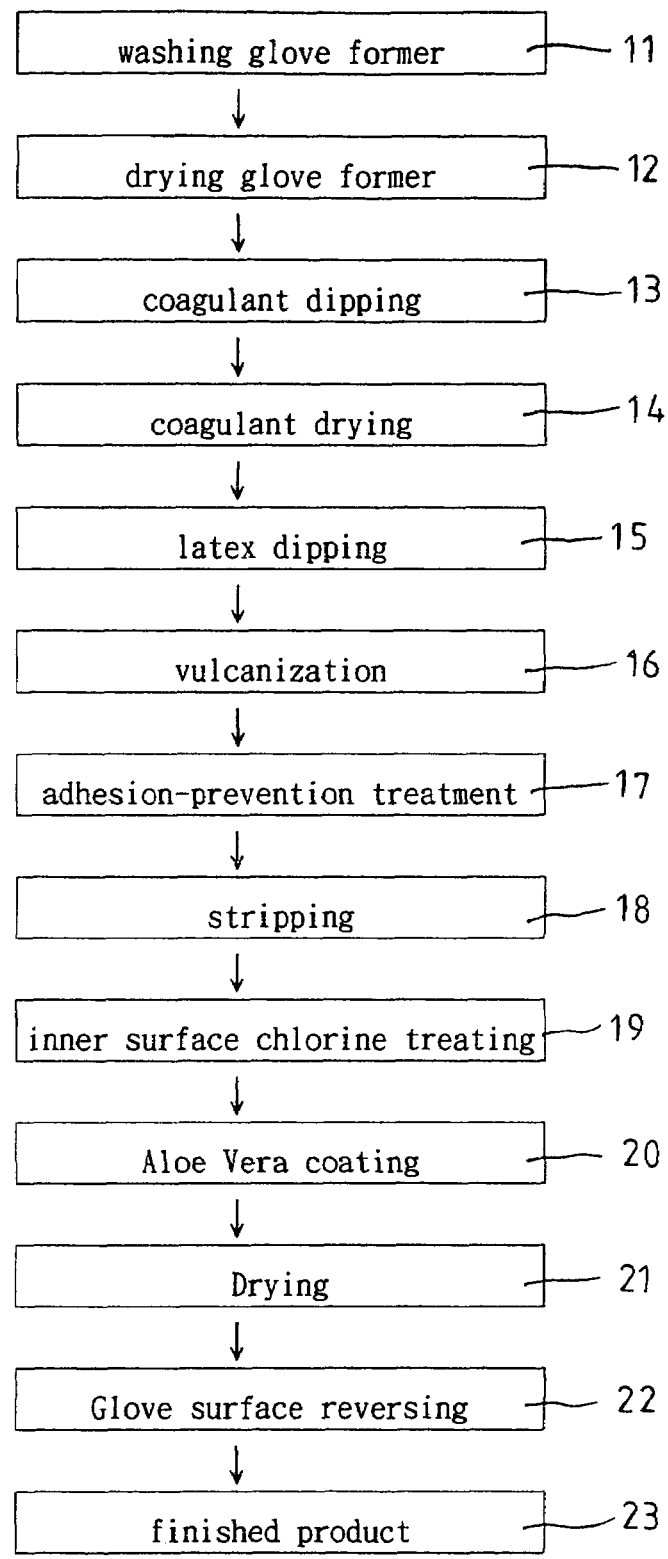
FIG. 2 is a block diagram showing a glove manufacturing flow according to the present invention.
Figure 3:
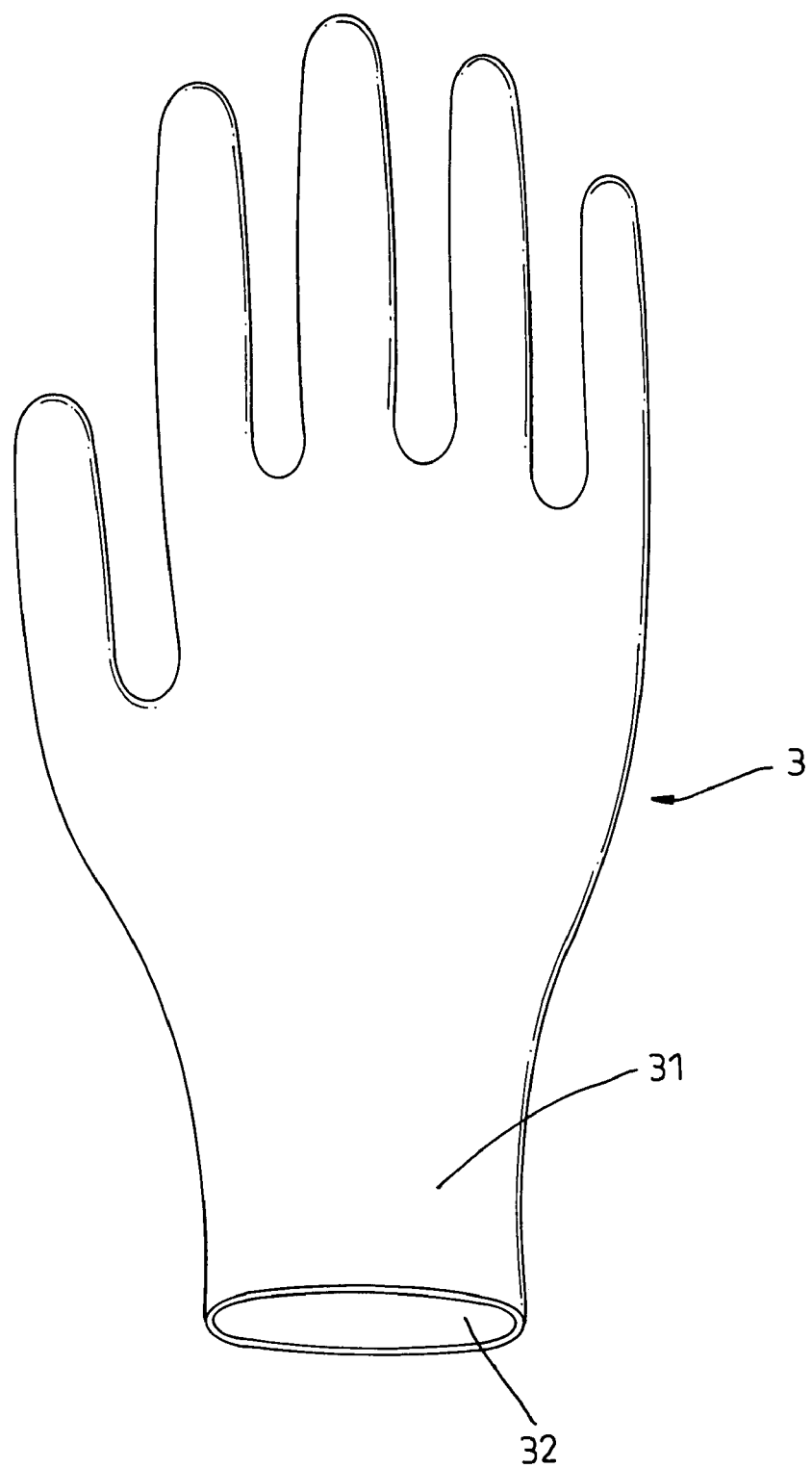
FIG. 3 is a perspective view of a glove removed from the respective glove former according to the present invention.

Referring to FIGS. 2~6, an Aloe Vera glove manufacturing method in accordance with the present invention comprises the steps of:

a) washing glove formers (11) where a cleaner is used to wash glove formers that are being carried on a conveyer with cleaning water or detergent;

b) drying glove formers (12) where the glove formers are dried in a baking oven at 100° C. (normally 100° C.±20° C.);

c) coagulant dipping (13) where the glove formers are dipped in a coagulant trough and coated with an evenly distributed layer of coagulant for easy adhesion of latex in a latter step;

d) coagulant drying (14) where the coagulant-coated glove formers are dried in a baking oven at 100° C. (normally 100° C.±20° C.);

e) latex dipping (15) where the coagulant-coated glove formers are dipped in a latex trough and coated with an evenly distributed layer of latex, and then the latex-coated glove formers are dried in a baking oven;

f) vulcanization (16) where the latex coating on each glove former is vulcanized at 120° C. (normally 120° C.±20° C.) to enhance elasticity, thereby forming a respective glove 3;

g) adhesion-prevention treatment (17) where the glove 3 with the respective glove former are dipped in wet powdering or coated with a layer of polymer coating to prevent adhesion of the inner layer of the glove 3 upon removal from the respective glove former;

h) stripping (18) where the gloves 3 are removed from the respective glove formers; and i) chlorine treating (19) where a chlorine treatment is applied to the gloves 3 by bringing the gloves into an environment containing chlorine, i.e., removing residual powders from the gloves 3 with chlorine solution of chlorine gas.

Figure 4:
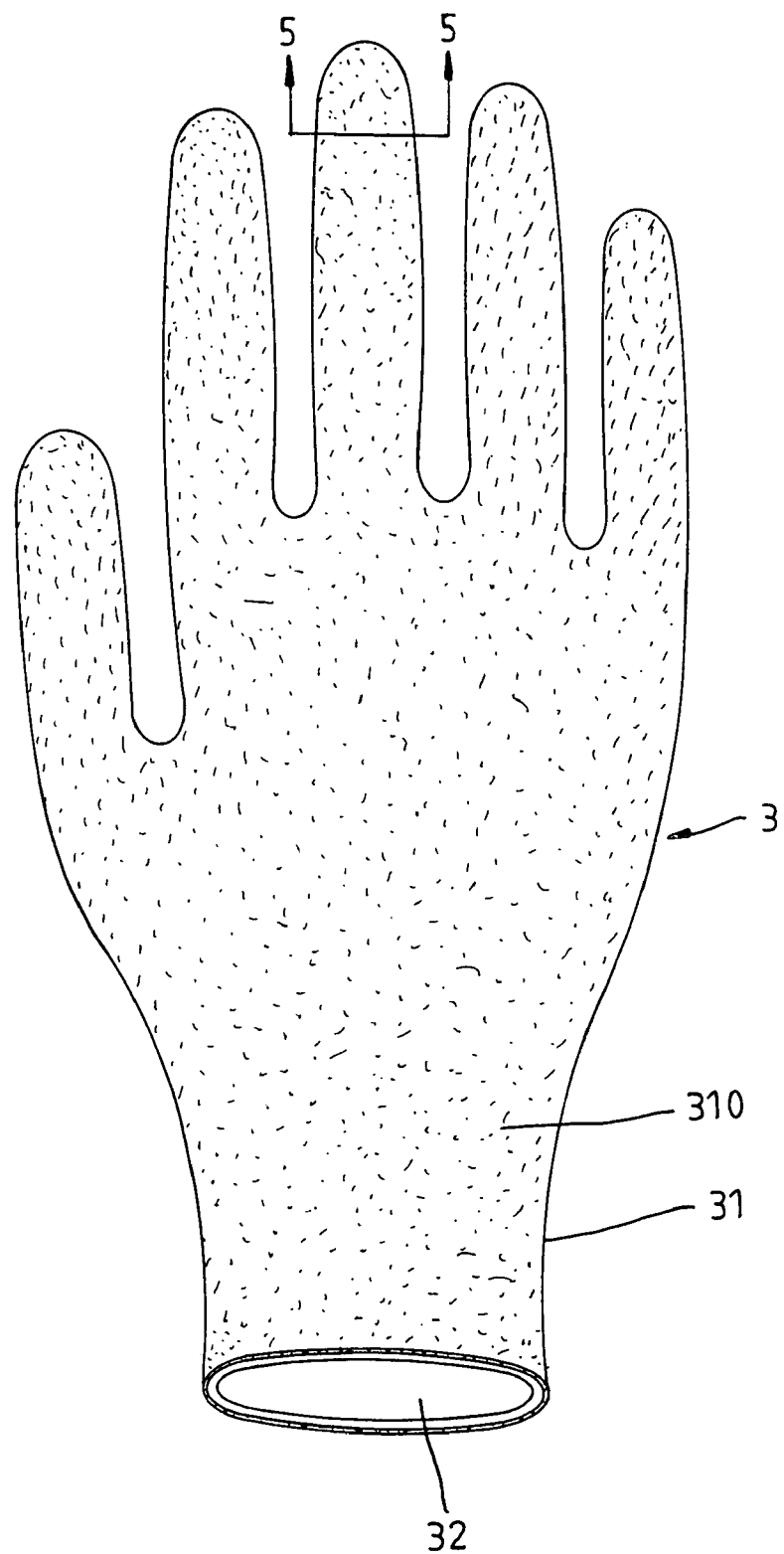
FIG. 4 is a perspective view of an Aloe Vera coated glove according to the present invention before the step of glove surface reversing.
Figure 5:
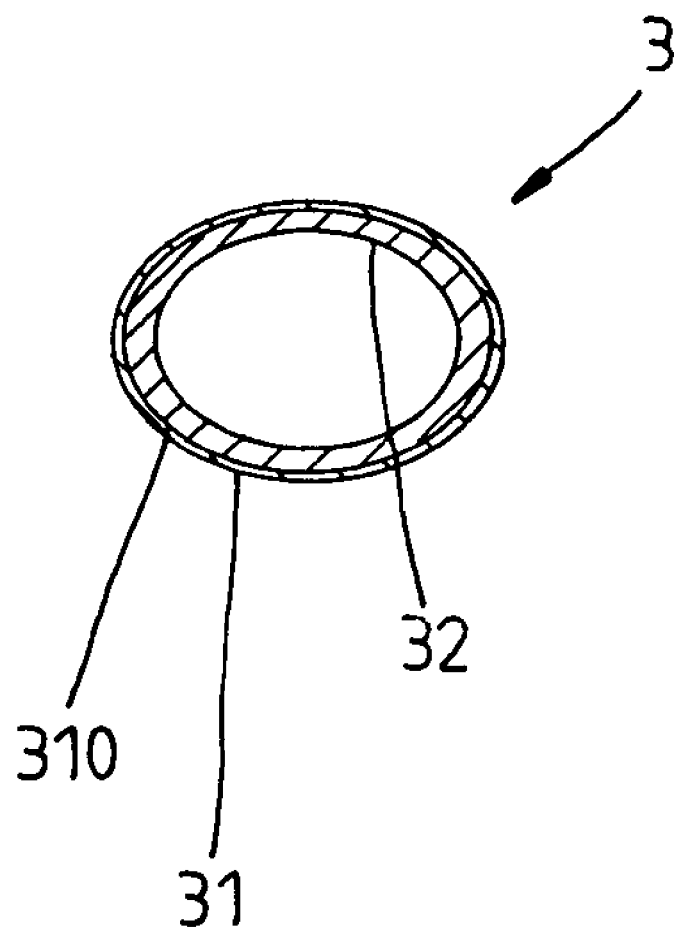
FIG. 5 is a sectional view taken along line 5-5 of FIG. 4.
Figure 6:
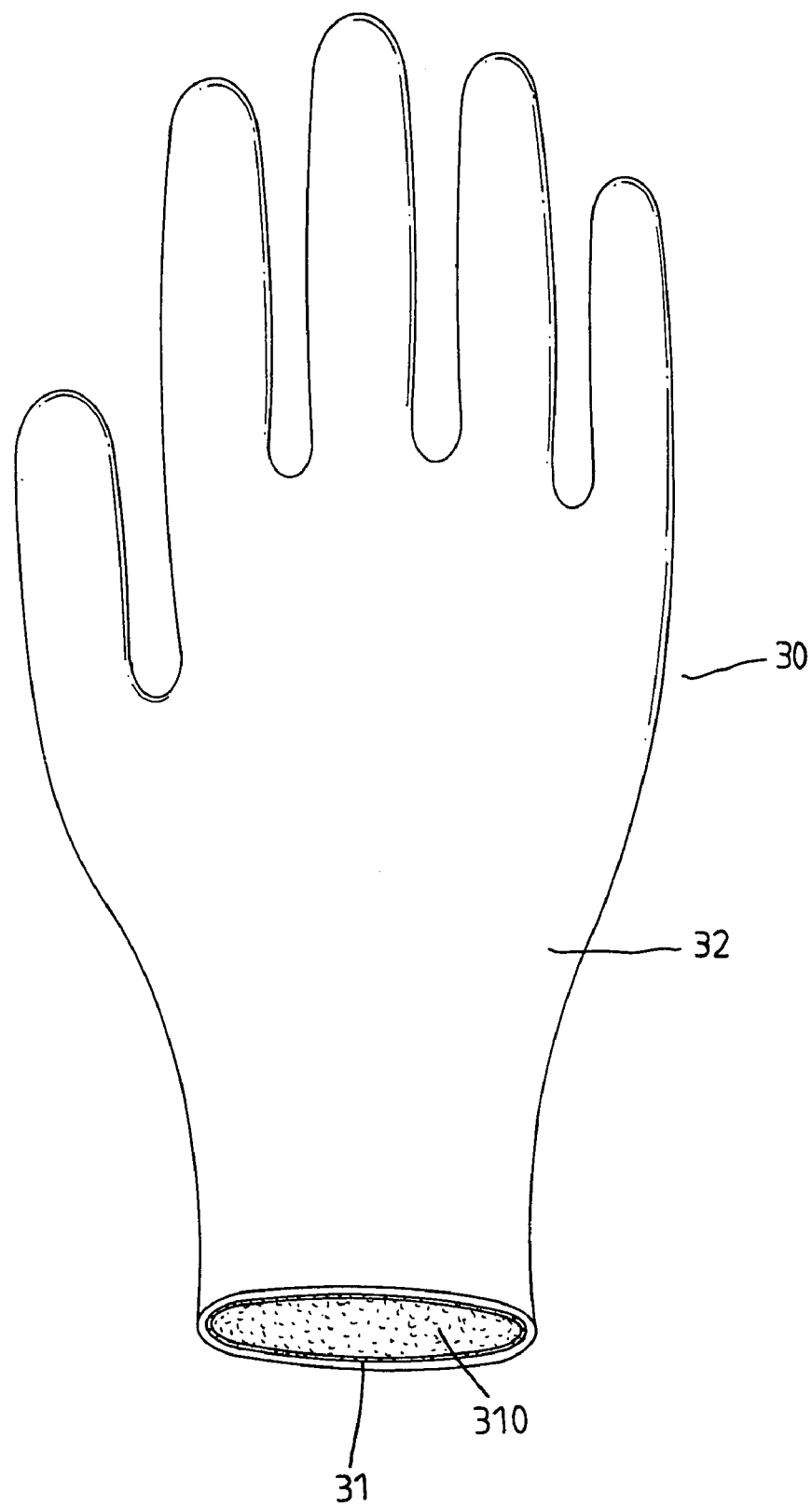
FIG. 6 is a perspective view of a finished Aloe Vera glove according to the present invention.

The main features of the present invention are outlined hereinafter. During step h) stripping (18), a flow of compressed air is employed to blow the gloves 3 away from the respective glove formers, keeping each glove 3 have the same status as the glove on the respective former whereby the inner surface 31 of each glove 3 faces outward and the outer surface 32 of each glove 3 face inward, wherein the inner surface 31 is the surface of the glove 3 that would face inward toward a hand while the glove is being worn on the hand. The inner-surface-out gloves 3 are then treated with chlorine treatment (19). The invention further comprises the steps:

j) Aloe Vera coating (20) where a layer of Aloe Vera (Aloe Vera solution) 310 is evenly coated on the inner surface 31 of each glove 3 by spraying or immersion (see FIGS. 4 and 5);

k) drying (21) where the gloves 3 are heated to cause water in the layer of Aloe Vera 310 to evaporate;

l) glove face reversing (22) where the Aloe Vera-coated gloves 3 are turned outside in to have the layer of Aloe Vera 310 coated inner surface 31 of each glove 3 face inward and the outer surface 32 of each glove 3 face outward (see FIG. 6);

m) finished product (30). After the aforesaid steps, the desired finished gloves 30 are obtained. When wearing the finished gloves 30 on the hands, the layer of Aloe Vera 31 of each finished glove 30 is kept in contact with the user's skin.

Further, the Aloe Vera solution used in the aforesaid glove manufacturing method is prepared by dissolving Aloe Vera gel in distilled water.

As indicated above, the invention has the following advantages:

1. Before stripping from the glove formers, the inner surface 31 of each glove 3 on the respective glove former faces outward, therefore the inner surface 31 of each glove 3 is maintained on the outside and the outer surface 32 of each glove 3 remained on the inside for quick chlorine treatment when removed from the respective glove former by a flow of compressed air. During the chlorine treating, the outer surface is remained inside. Chlorine solution is forced to react with the inner surface 31 first, then the cuff portion and the palm portion of the outer surface 32 before it can reach the finer tip portions of the outer surface 32 (see FIG. 3). Chlorination is a quick and fast reaction, when the chlorine solution finally reaches the finger tip portions of the outer surface, its strength has been weakened. Consequently, the chance to overdo the chlorination has been significantly reduced. This method prevents overdone of chlorine treatment at the tips of the finger portions of the outer surface 32 of the gloves 3. Therefore, when the users use the finished gloves 30 to perform a medical operation, the finger portions of the outer surface 32 of the finished gloves 30 do not slip on holding, and the users can operate medical instruments safely.

2. The procedure from stripping (18) to the finished product 30 is quite simple and eliminates the steps of (49) and (50) as disclosed in the U.S. Pat. No. 6,274,154; therefore the invention greatly improves the manufacturing efficiency and reduces the manufacturing cost.

3. When in use, the layer of Aloe Vera is maintained in contact with the user's skin, and the active ingredients in Aloe Vera can then condition hand skin and prevent microorganisms from growing under the wet condition.

While only one embodiment of the present invention has been shown and described, it will be understood that various modifications and changes could be made thereunto without departing from the spirit and scope of the invention disclosed.

What is claimed is:

1. An Aloe Vera glove manufacturing method comprises the steps of:

a) using a cleaner to wash glove formers being carried on a conveyer with a cleaning solution;

b) drying said glove formers by heating;

c) dipping said glove formers in a coagulant trough so as to coat said glove formers with an evenly distributed layer of coagulant forming coagulant-coated glove formers;

d) drying said coagulant-coated glove formers by heating;

e) coating said coagulant-coated glove formers with an evenly distributed layer of latex and then drying the latex coating by heating;

f) vulcanizing the latex coating on each glove former of the glove formers by heating, thereby forming a glove on each glove former, each glove is located in an inverted position and has an inner surface facing outwardly and an outer surface facing inwardly and contacting a corresponding glove former;

g) covering the glove on each glove former with a layer of adhesion-prevention coating;

h) removing each glove from the corresponding glove former utilizing a flow of compressed air to separate each glove from the corresponding glove former while maintaining the inverted position of the glove with the inner surface facing outwardly and the outer surface facing inwardly;

i) treating each glove with a chlorine treatment once while the inner surface of the glove faces outwardly;

j) covering a layer of Aloe Vera solution on the inner surface of each glove;

k) drying said aloe Vera solution on the inner surface of each glove by heating to form Aloe Vera-coated gloves; and l) arranging said Aloe Vera-coated gloves to have the layer of Aloe Vera coating the inner surface of each glove facing inwardly and the outer surface of each glove facing outwardly, wherein said Aloe Vera-coated gloves produced by said steps (a) through (l) are only treated with chlorine once, said single chlorine treatment being applied only when the inner surface of said Aloe Vera-coated gloves produced by said steps (a) through (l) is facing outwards, and wherein said Aloe Vera-coated gloves produced by the steps (a) through (l) have a friction force on the outside surface higher than 0.5 lb making handling medical instruments more secure.

2. The Aloe Vera glove manufacturing method as claimed in claim 1, wherein the layer of adhesion-prevention coating is a polymer coating minimizing a need for chlorination and reducing surface tackiness of the glove.

3. The Aloe Vera glove manufacturing method as claimed in claim 1, wherein said step i) treating said gloves with a chlorine treatment is done by applying chlorine gas to said gloves to remove residual solid matter and to reduce tackiness from said gloves.

4. An Aloe Vera glove manufacturing method consisting of the steps of:
- a) using a cleaner to wash glove formers being carried on a conveyer with a cleaning solution;
- b) drying said glove formers by heating;
- c) dipping said glove formers in a coagulant trough so as to coat said glove formers with an evenly distributed layer of coagulant forming coagulant-coated glove formers;
- d) drying said coagulant-coated glove formers by heating;
- e) coating said coagulant-coated glove formers with an evenly distributed layer of latex and then drying the latex coating by heating;
- f) vulcanizing the latex coating on each glove former of the glove formers by heating, thereby forming a glove on each glove former, each glove is located in an inverted position and has an inner surface facing outwardly and an outer surface facing inwardly and contacting a corresponding glove former;
- g) covering the glove on each glove former with a layer of adhesion-prevention coating;
- h) removing each glove from the corresponding glove former utilizing a flow of compressed air to separate each glove from the corresponding glove former while maintaining the inverted position of the glove with the inner surface facing outwardly and the outer surface facing inwardly;
- i) treating each glove with a chlorine treatment once while the inner surface of the glove faces outwardly;
- j) covering a layer of Aloe Vera solution on the inner surface of each glove;
- k) drying said aloe Vera solution on the inner surface of each glove by heating to form Aloe Vera-coated gloves; and
- l) arranging said Aloe Vera-coated gloves to have the layer of Aloe Vera coating the inner surface of each glove facing inwardly and the outer surface of each glove facing outwardly.

5. The Aloe Vera glove manufacturing method as claimed in claim 4, wherein said Aloe Vera-coated gloves produced by the steps (a) through (l) have a friction force on the outside surface higher than 0.5 lb making handling medical instruments more secure.

* * * * *